United States Patent [19]

Sturgill

[11] Patent Number: 4,701,612

[45] Date of Patent: Oct. 20, 1987

[54] INSPECTION OF CONTAINER FINISH

[75] Inventor: Dennis T. Sturgill, Toledo, Ohio

[73] Assignee: Owens-Illinois, Inc., Toledo, Ohio

[21] Appl. No.: 756,539

[22] Filed: Jul. 19, 1985

[51] Int. Cl.$^4$ ............................................. G01N 21/90
[52] U.S. Cl. ................................. 250/223 B; 209/526; 356/240; 358/106
[58] Field of Search ................... 250/223 B; 356/237, 356/239, 240; 358/106; 209/524–526, 529

[56] References Cited

U.S. PATENT DOCUMENTS 4,064,534  12/1977  Chen et al. ........................... 358/106
4,601,395   7/1986  Juvinall et al. ...................... 356/240

FOREIGN PATENT DOCUMENTS 2036301   6/1980  United Kingdom .
2096763  10/1982  United Kingdom .
2135769   9/1984  United Kingdom .

Primary Examiner—Edward P. Westin
Attorney, Agent, or Firm—H. G. Bruss

[57] ABSTRACT

Apparatus and method for inspecting the finish of transparent containers, particularly glass containers, which include facility for directing diffused light energy laterally through the container finish as the container is rotated about its central axis. A camera includes a plurality of light sensitive elements disposed in a linear array angulated with respect to the container axis to view the external and internal finish wall surfaces, the latter through the open container mouth. Individual elements of the camera linear array are sampled by an information processor at increments of container rotation, and corresponding data indicative of light intensity at each element is stored in an array memory as a combined function of element number and scan increment. Such data is compared following completion of container rotation to standard data indicative of acceptable container finish, and a reject signal is generated if such comparison exceeds an operator adjustable threshold.

5 Claims, 3 Drawing Figures

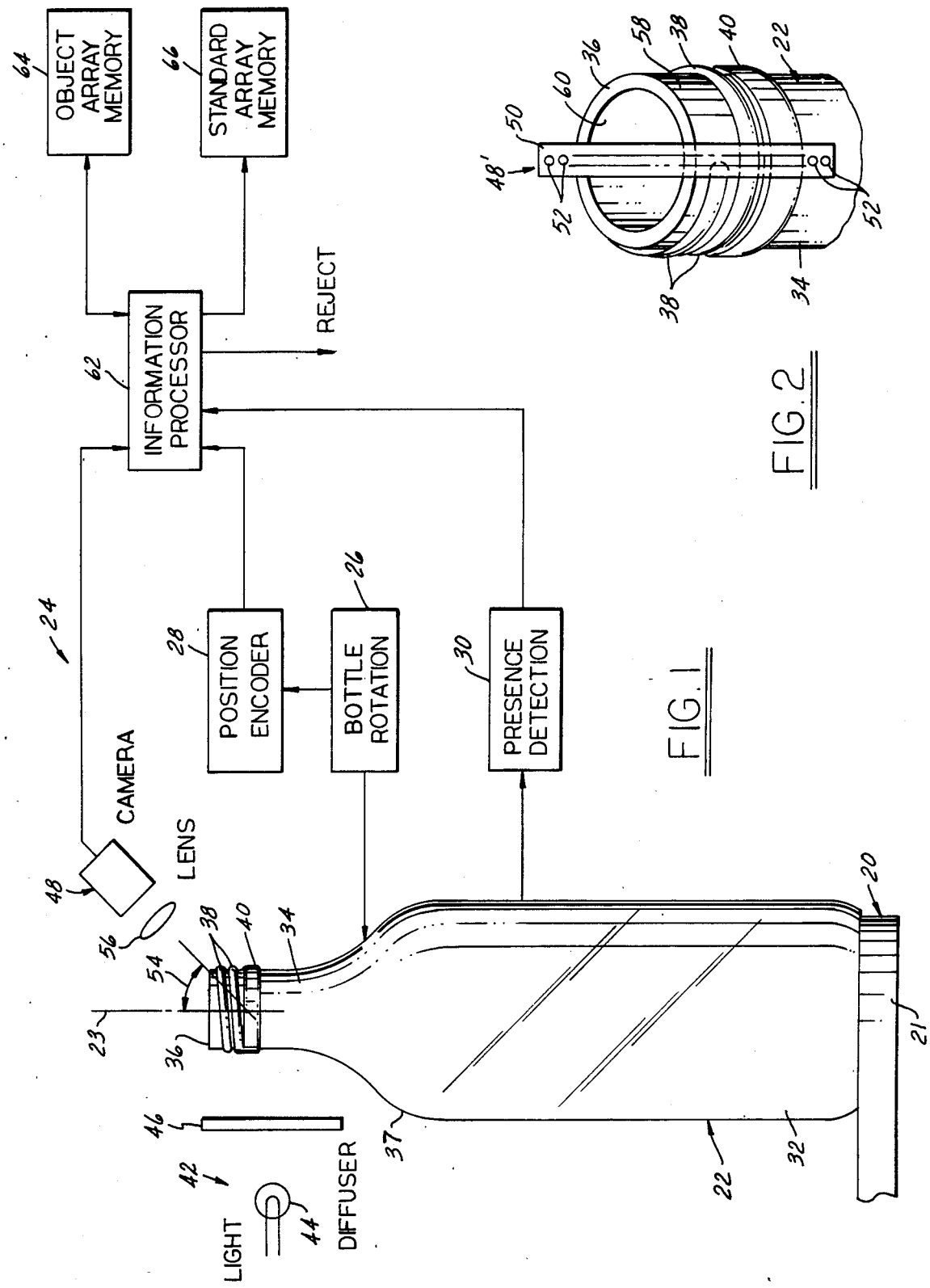

INSPECTION OF CONTAINER FINISH

The present invention is directed to inspection of containers, and more particularly to methods and apparatus for inspecting the finish of containers for finish defects.

BACKGROUND OF THE INVENTION

In the art of container manufacture, the term "container finish" generally refers to that portion of the container which defines the container mouth. In a bottle, for example, the finish includes that portion of the container neck having threads and/or shoulders for receiving the container cap, as well as the upper surface of the neck surrounding the container mouth against which the cap seats. It is important that the container finish be properly manufactured so that a cap may be affixed thereto to seal the container cavity against leakage and escape of carbonation, etc. during handling and storage.

Conventional technology for mass production of glass or plastic containers involves forming the containers in a multiplicity of blow-molds. Various types of defects may occur. It has heretofore been proposed to employ optical scanning techniques for inspecting such containers for defects which affect optical transmission characteristics of the container side wall. In U.S. Pat. Nos. 4,378,493, 4,378,494 and 4,378,495, all of which are assigned to the assignee of the present application, there is disclosed a method and apparatus in which glass containers are conveyed through a plurality of positions or stations where they are physically and optically inspected. At one optical inspection station, a glass container is held in vertical orientation and rotated about its vertical central axis. An illumination source directs diffused light energy through the container side wall. A camera, which includes a plurality of light sensitive elements, i.e., pixels, oriented in a linear array parallel to the vertical axis of container rotation, is positioned to view light transmitted through a vertical strip of the container side wall. The output of each pixel is sampled at increments of container rotation, and event signals are generated when the magnitude of adjacent pixel signals differ by more than a preselected threshold level. An appropriate reject signal is thus produced and the defective container is sorted from the conveyor line.

OBJECTS AND SUMMARY OF THE INVENTION

It is a general object of the present invention to provide an apparatus and method for inspecting the finish of a container as a function of the optical characteristics thereof, and for indicating that the container under inspection should be rejected when such optical characteristics do not meet a predetermined standard.

A more particular object of the invention is to provide a container finish inspection apparatus and method of the described character wherein optical transmission characteristics of a test container are obtained and compared with corresponding characteristics of a standard acceptable container, and wherein a reject signal is provided where such comparison indicates that the test container is unacceptable.

A further object of the invention is to provide a container finish inspection apparatus and method of the described character which are economical to implement in mass production of containers, and which may be readily implemented in combination with inspection of the container body for side wall defects and the like.

In accordance with the present invention, the finish of a container of transparent glass or plastic manufacture is inspected by directing a source of diffused light energy onto the container from a lateral direction while the container is held stationary and rotated about its central axis. A camera, which includes a plurality of light sensitive elements disposed in a linear array coplanar with the container axis of rotation, is positioned at a downward angle with respect to the container axis to view diametrically opposite portions of the inside and outside surfaces of the finish wall which surrounds the container mouth. The camera elements are scanned at increments of container rotation, and information indicative of light intensity at each camera element is stored in a first memory as an array by element number and scan increment. Thus, the camera views both the inside and outside surfaces of the finish wall as the container is rotated, and corresponding finish information is stored in memory.

Following termination of a complete container finish scan, test information stored in memory is compared with standard information stored in a second memory indicative of an acceptable container finish. Such standard information in the preferred embodiment of the invention is obtained in a set-up operation by scanning a standard container predetermined to possess an acceptable finish and storing such information in an array by camera element and scan increment. The test and standard memory arrays may then be compared to each other, and a reject signal generated when such comparison indicates a difference which exceeds a preselected operator adjustable threshold.

In the preferred embodiment of the invention, the camera and light source are positioned on opposite sides of the container axis. Light energy "seen" by the camera is thus a complex function which depends upon the refractive characteristics of the container under test. It will be appreciated, however, that such characteristics will be generally similar for a given container configuration, with some differences associated with manufacturing tolerances, differing forming molds and differing glass runs. It is contemplated that the threshold difference between the test and standard information arrays which results in a reject signal is to be empirically determined by the operator.

BRIEF DESCRIPTION OF THE DRAWINGS

The invention, together with additional objects, features and advantages thereof, will be best understood from the following description, the appended claims and the accompanying drawings in which:

FIG. 1 is a schematic diagram of apparatus for inspecting the finish of containers in accordance with a presently preferred embodiment of the invention;

FIG. 2 is a schematic illustration of the container finish as viewed by the camera, with camera field of view superimposed thereon.

DETAILED DESCRIPTION OF PREFERRED EMBODIMENT

Figure 3:
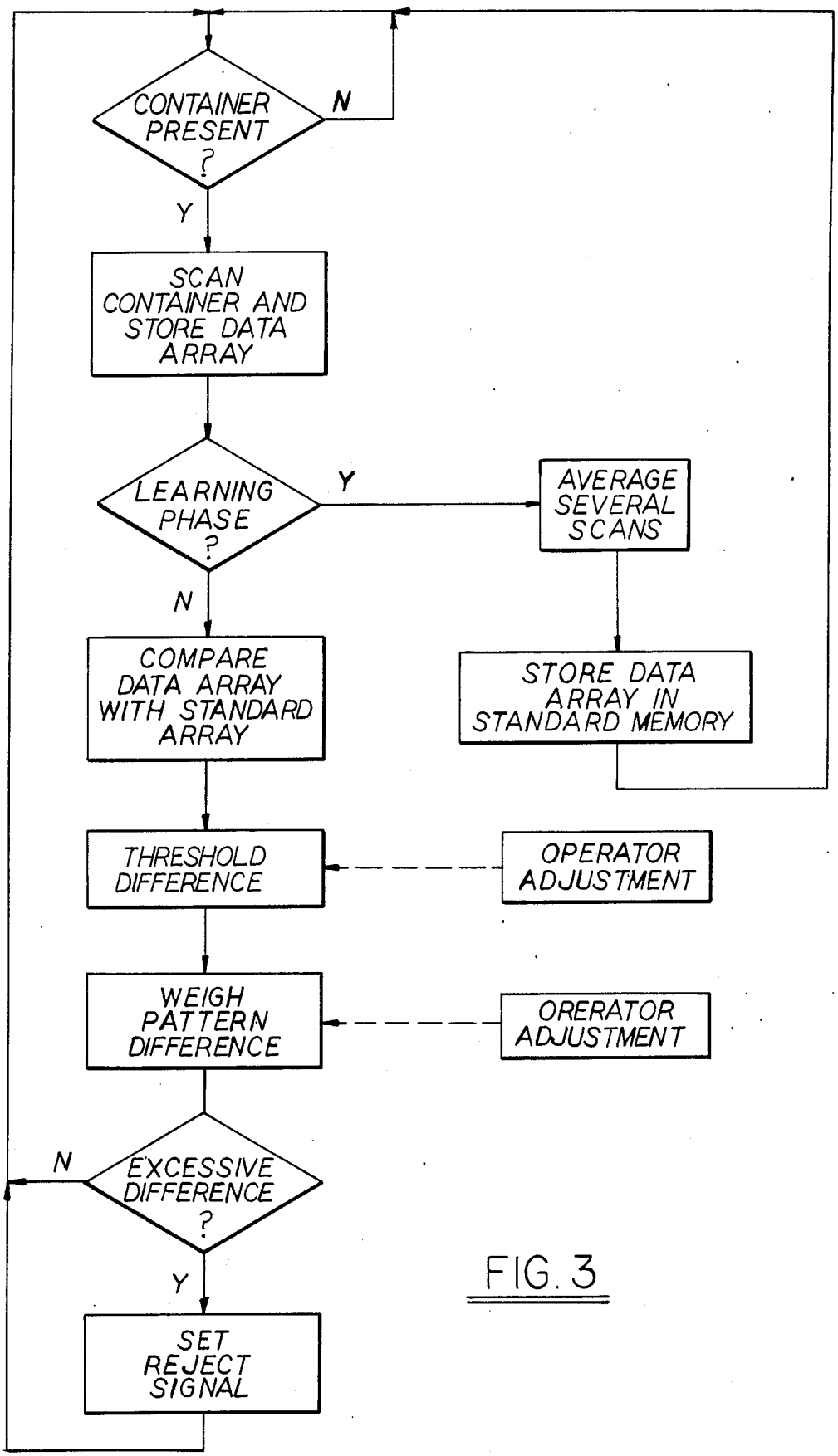
FIG. 3 is a flow chart which illustrates operation of the invention for inspection of container finish.

Referring to FIG. 1, a conveyor 20, typically including a starwheel (not shown) and a slide plate 21, is so disposed and connected to a source of molded containers as to bring successive containers 22 into position at a finish inspection station 24. Conveyor 20 may be of any suitable type, such as those shown in U.S. Pat. Nos. 4,230,219 and 4,378,493, the disclosures of which are incorporated herein by reference, and would typically include a rotatable starwheel for bringing successive containers into position and holding the containers in fixed position during the scanning operation. A bottle rotating device 26 such as a drive roller is positioned to engage container 22 at station 24 and to rotate the container about its central axis 23. An encoder 28 is coupled to the container rotation mechanism to provide signals indicative of increments of container rotation. A detector 30, such as a limit switch, is positioned to provide a signal indicative of presence of container 22 at station 24.

In the preferred implementation of the invention herein discussed, container 22 is illustrated as a molded glass bottle having a container body 32 and a generally cylindrical neck 34 which projects upwardlly from the body shoulder 37. The portion of the container finish inspected in accordance with the present invention includes the upper portion of neck 34 which terminates in a cap sealing surface 36. A helical thread 38 is integrally molded onto the outer surface of the finish wall which surrounds the container mouth, and a lip or shoulder 40 is likewise formed on the finish wall outer surface over which a cap skirt may be crimped in the usual manner for affixing the cap to the container. In general, the present invention is adapted to inspect that portion of the container finish to which the cap is to be affixed.

A light source 42 is positioned to direct diffused light energy onto the container finish from a direction generally lateral to container axis 23. Light source 42 includes one or more lamps 44 and a diffuser plate 46. A camera 48 is positioned on the side of axis 23 opposite to light source 42. Camera 48 includes a plurality of light sensitive elements or pixels 52 (FIG. 2) disposed in a linear array 50 having a lengthwise dimension coplanar with axis 23 and directed downwardly toward the container mouth at an angle 54 with respect to the container axis. A lens 56 focuses the field of view of camera linear array 50 in the manner illustrated in FIG. 2 so as to view diametrically opposite portions of the coaxial cylindrical container finish external and internal wall surfaces 58,60, internal wall surface 60 being viewed at angle 54 through the open container mouth. (It will be appreciated that the effective image 48' of camera 48 is illustrated in FIG. 2.) In a preferred embodiment of the invention, element array 50 includes two hundred fifty-six elements 52 having a composite linear field of view which extends at least from the opposite edge of sealing surface 36 to the adjacent lower edge of shoulder 40. (It will be appreciated, of course, that the invention is in no way limited to the particular finish configuration shown for illustration purposes in the drawings.)

An information processor 62 receives a signal from detector 30 indicative of presence of a container 22 at inspection station 24, and signals from encoder 28 indicative of increments of container rotation. Light sensitive elements 52 of camera array 50 are likewise individually coupled to information processor 62 for providing thereto respective signals indicative of the intensity of light incident on each element. Information processor 62 is connected to an object array memory 64 and to a standard array memory 66, and has an output for providing a reject signal to container sorting apparatus (not shown). Each array memory 64,66 is an N×M array memory, where N is equal to or greater than the number of elements or pixels 52 in camera array 50, and M is equal to or greater than the number of scan increments for one complete rotation of container 22. In the preferred embodiment of the invention, two hundred fifty-six elements or pixels 52 are provided in array 50, and two hundred fifty-six increments per container rotation are employed, each memory 64,66 thus containing an array of at least 256×256 memory word locations.

FIG. 3 is a flow chart which illustrates operation of information processor 62 for inspecting the finish of container 22. When a container 22 is detected at inspection station 24, information processor 62 scans each element 52 of camera array 50 at each increment of container rotation and stores information in object array memory 66 as a function of corresponding light intensity at each array element. During an initial or learning phase, container 22 is selected to possess a known acceptable container finish, and the information obtained in each scan is averaged over several scans and then stored in standard array memory 66. Standard array memory 66 thus contains a complete array of average intensities, by camera element and scan increment, for a container having an acceptable finish. During inspection of test containers, i.e. when station 24 is not in such learning phase, the object or test array in memory 64 is compared, following completion of container rotation and scan, with the corresponding standard information stored in memory 66.

It will be appreciated, of course, that although memories 64,66 contain corresponding arrays for comparison purposes, such arrays need not necessarily register with each other since container finish scans do not begin and end at a predetermined fixed position circumferentially of the container axis. Stated differently, each container scan begins at a random angular location circumferentially of the container axis. However, for a given container design configuration, the array patterns will remain substantially identical. It is therefore only necessary to translate or shift data stored in object array memory 64 until the pattern of data stored therein generally registers or corresponds with that stored in standard array memory 66, so that the data may then be compared to determine if individual or groups of data stored in object memory 64 indicate a defective container. Such comparison preferably includes a first comparison of data at individual array locations to determine if test and standard data differ from each other by an operator adjustable threshold difference. A second comparison is then implemented to determine if the average or weighted intensity of the entire data pattern differs from the standard pattern by more than an operator adjustable difference. If either or both of such comparisons indicate an excessive difference, the reject signal is set, and processor operation recycles to await receipt of a subsequent container at the inspection station.

Camera 48 and lens 56 (FIG. 1) are preferably mounted for adjustment of angle 54 with respect to container axis 23. Angle 54 is adjusted during a set-up operation as a function of container geometry, so that camera 48 will be able to view both the internal and external finish wall surfaces as described. Specifically, the viewing angle is determined by the height of the threads and the size of the mouth opening such that the thread area on the far side of the container is visible through the mouth and finish wall. As presently envisioned, angle 54 is preferably adjustable between at least 45° and 75°.

The invention claimed is:

1. A method of inspecting the finish of containers having an open mouth and a central axis, said method comprising the steps of:
   (a) selecting a standard container having an acceptable finish,
   (b) directing diffused light energy onto the finish of said standard container while holding said container with its axis in fixed position and rotating said standard container about its axis,
   (c) providing a camera which includes an array of light sensitive elements in a line coplanar with said central axis and oriented at an angle to said axis across said axis from said light source so as to view both inside and outside surfaces of said standard container finish,
   (d) scanning said linear array at preselected increments of container rotation and storing in memory information indicative of intensity of light at each said element in a two-dimensioal standard data array as a function of said increments,
   (e) selecting a test container having unknown finish characteristics,
   (f) directing diffused light energy onto the finish of said test container while holding said test container with its axis in fixed position and rotating said test container about its axis,
   (g) providing a camera which includes a linear array of light sensitive elements equal in number to elements in said camera of step (c), oriented coplanar with said axis of said test container at an angle thereto identical to said angle in step (c),
   (h) scanning said linear array of step (g) at the same said preselected increments of container rotation and storing in memory information indicative of intensity of light at each said element in a two-dimensional object data array as a function of said increments,
   (i) comparing information stored in said standard and object data arrays, and
   (j) providing a signal when information stored in said standard and object data arrays differs by more than a preselected threshold.

2. The method set forth in claim 1 wherein said step (i) includes the step of translating data in said object array until patterns of data in said object and standard arrays substantially coincide.

3. The method set forth in claim 2 wherein said step (i) includes the further step of comparing data stored at individual locations in said two-dimensional object array to data stored at corresponding individual locations in said two-dimensional standard array.

4. The method set forth in claim 3 wherein said step (i) includes the additional step of comparing average data stored in the entire said object array to average data stored in the entire said standard array.

5. The method set forth in claim 1 wherein said steps (b)–(c) and said steps (f)–(g) are carried out at a single test station, said light sources in said steps (b) and (f) being the same and cameras in said steps (c) and (g) being the same.

* * * * *